(12) United States Patent
Woodruff et al.

(10) Patent No.: US 8,192,368 B2
(45) Date of Patent: Jun. 5, 2012

(54) PRESSURE SENSING CATHETER

(75) Inventors: David M. Woodruff, Dallas, TX (US); Phillip M. Leopold, North Barrington, IL (US)

(73) Assignee: Gentera Holdings, LLC, Dover, NH (US)

( * ) Notice: Subject to any disclaimer, the term of this patent is extended or adjusted under 35 U.S.C. 154(b) by 389 days.

(21) Appl. No.: 12/480,307

(22) Filed: Jun. 8, 2009

(65) Prior Publication Data

US 2009/0306539 A1 Dec. 10, 2009

Related U.S. Application Data

(60) Provisional application No. 61/059,992, filed on Jun. 9, 2008.

(51) Int. Cl.
*A61B 5/00* (2006.01)
(52) U.S. Cl. ........................................ 600/561
(58) Field of Classification Search .................. 600/561
See application file for complete search history.

(56) References Cited

U.S. PATENT DOCUMENTS

| | | | |
|---|---|---|---|
| 4,136,681 A | 1/1979 | Hon | |
| 4,160,448 A | 7/1979 | Jackson | |
| 4,252,131 A | 2/1981 | Hon et al. | |
| 4,600,015 A | 7/1986 | Evans et al. | |
| 4,924,877 A | 5/1990 | Brooks | |
| 4,944,307 A | 7/1990 | Hon et al. | |
| 6,447,462 B1 | 9/2002 | Wallace et al. | |
| 2003/0195428 A1 * | 10/2003 | Brockway et al. | 600/486 |

FOREIGN PATENT DOCUMENTS

| | | |
|---|---|---|
| DE | 19532332 A1 | 4/1996 |
| DE | 19530440 A1 | 2/1997 |
| WO | WO2008012802 A2 | 1/2008 |

* cited by examiner

*Primary Examiner* — Jeffrey G Hoekstra
(74) *Attorney, Agent, or Firm* — William A. Loginov, Esq.; Loginov & Associates, PLLC

(57) ABSTRACT

This invention provides a pressure sensing catheter, and method for using the same, which eliminates the practitioners' need to fill the catheter with fluid manually prior to insertion, and thereby increases the accuracy and ease of the overall pressure-sensing procedure. The illustrative catheter includes, in its proximal end, a transducer base or housing that is permanently attached to the catheter shaft. The base includes, inserted thereinto, one or more miniaturized pressure transducer assemblies, which are in fluid communication with corresponding pressure lumens that extend down the shaft and are in communication with one or more predetermined balloons by discrete channels or ports, which provide a fluid passage between the interior space of the balloon and the corresponding pressure lumen. The integral assembly includes a predetermined, previously installed charge of fluid that extends from the transducer, through the corresponding pressure lumen and into the interior volume of the sensing balloon. The charge of fluid has been made free of any air bubbles at the point of manufacture, and is delivered fully charged, so that maximum sensing accuracy and minimum setup time are achieved. In alternate embodiments the catheter can include a fluid infusion/flushing lumen and port interconnected to a proximal fluid connection.

20 Claims, 13 Drawing Sheets

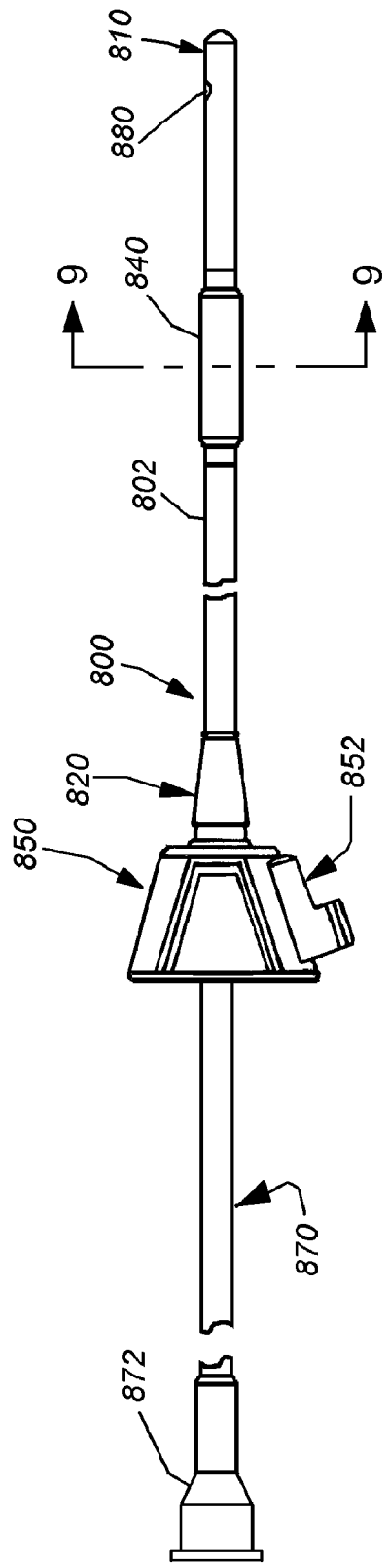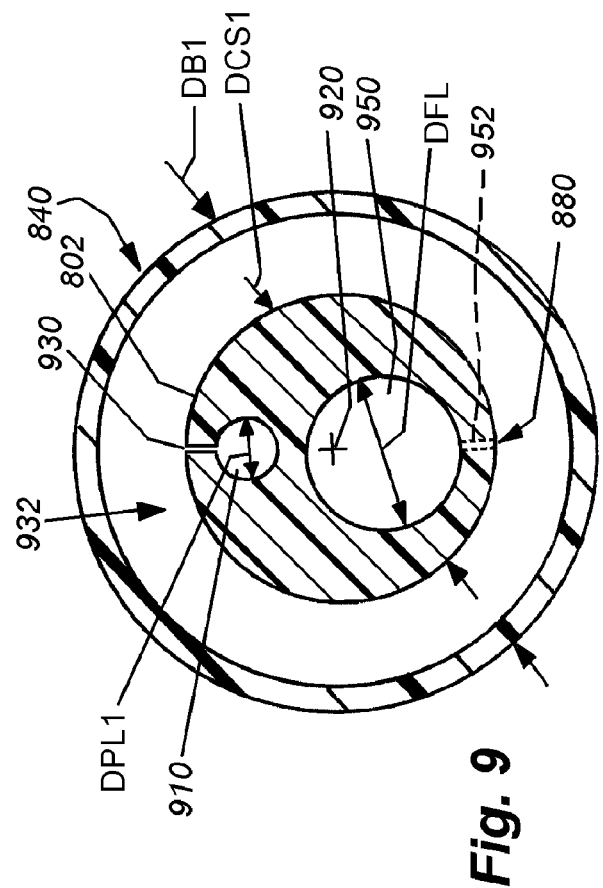

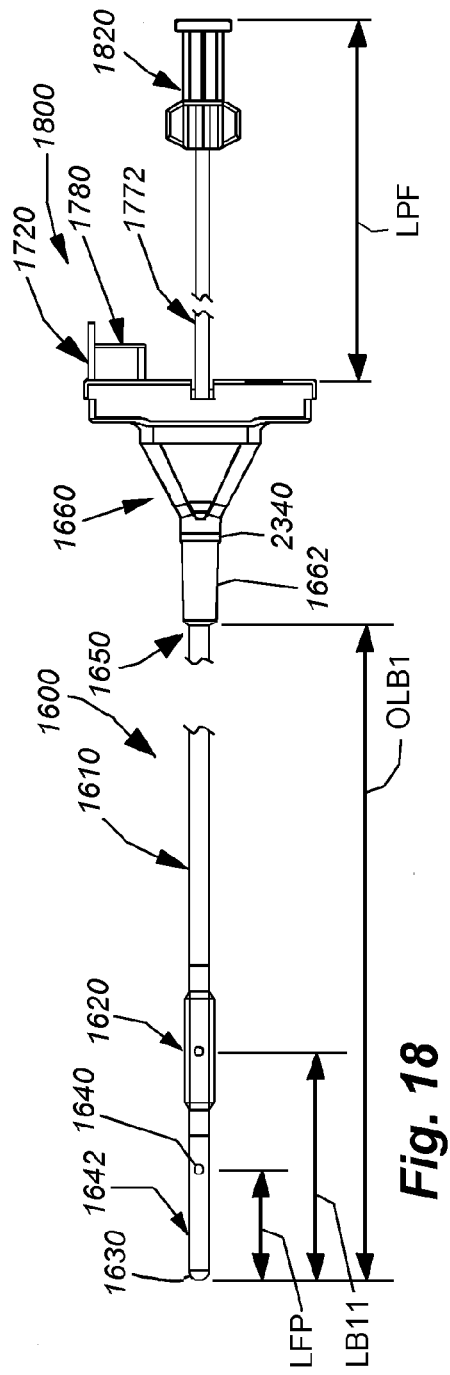
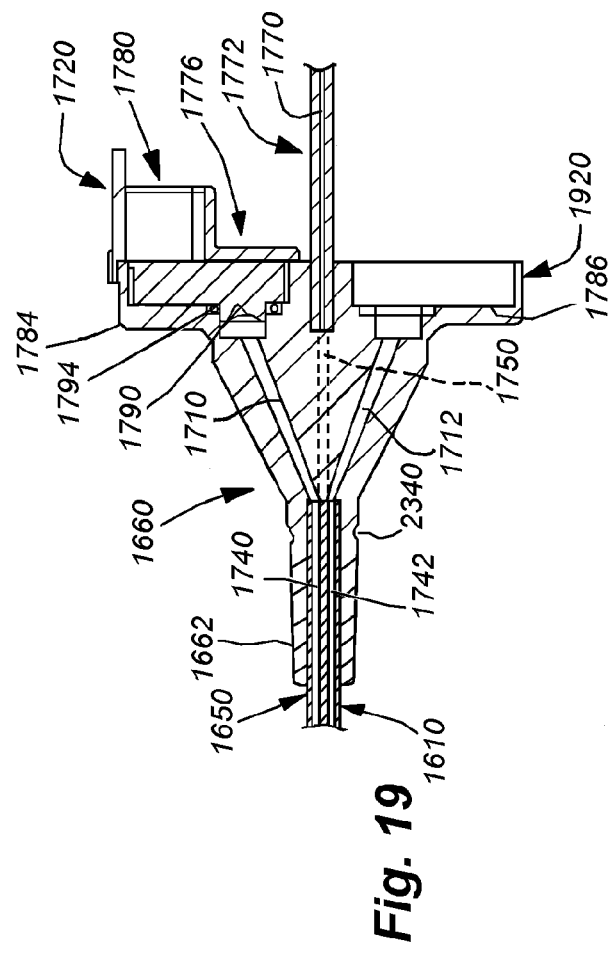
Fig. 18
Fig. 19

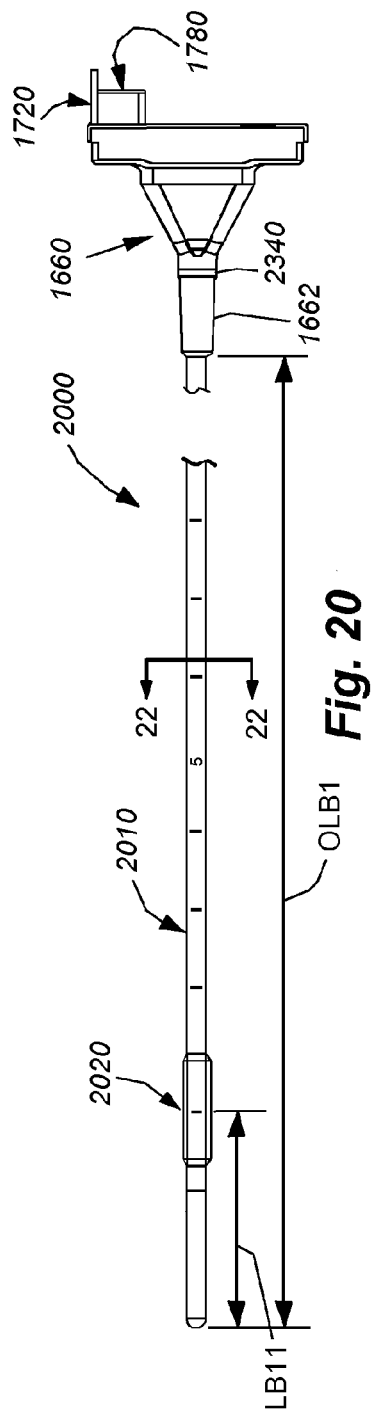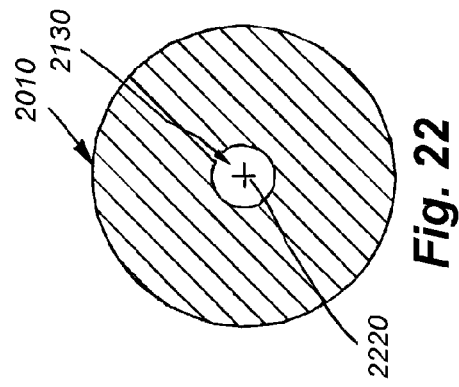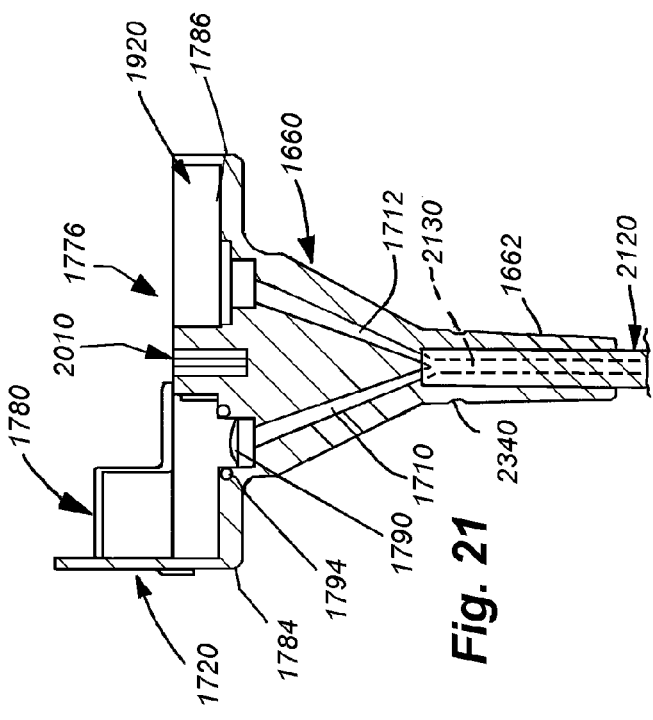

PRESSURE SENSING CATHETER

RELATED APPLICATIONS

This application claims the benefit of U.S. Provisional Application Ser. No. 61/059,992, filed Jun. 9, 2008, entitled PRESSURE SENSING CATHETER, the entire disclosure of which is herein incorporated by reference.

FIELD OF THE INVENTION

This invention relates to catheters for sensing the pressure of internal body regions.

BACKGROUND OF THE INVENTION

Pressure sensing catheters are used in a variety of medical procedures. Such catheters can be employed to sense pressure in rectal or urodynamic applications, being positioned within the urethra or bladder or another internal location within the body. Pressure-sensing catheters may also be applied to the rectum, vagina, or another internal location within the body in which pressure readings are desired. With reference to FIG. 1, a pressure sensing catheter 100 according to a typical prior art implementation is shown. In this example, the catheter 100 has been inserted transurethrally into the subject patient's bladder 110. While not shown, it can be assumed that the bladder is filled with urinary fluid under predetermined pressure that may be in excess or ambient atmospheric pressure. The catheter shaft 101 may be 7 French in diameter (approximately 0.096 inch), allowing it to pass relatively easily through the urethra. The distal end 112 of the exemplary catheter 100 includes a single pressure-sensing balloon 114 according to the prior art. The balloon is pliable, polymeric membrane that defines a predetermined interior space with respect to the underlying, semi-rigid catheter shaft 101. The balloon 114 is attached in a fluid-tight manner to the catheter shaft's outer surface using adhesives or another attachment technique. The interior space of the balloon 114 (defined between the catheter's outer surface and the balloon's inner wall) communicates with an inner lumen (not shown) that allows fluid/pressure to pass between the balloon enclosure and the proximal end 116 of the catheter 100.

The catheter's proximal end 116 includes a standard fitting 120 that is sized and arranged to receive the fluid-dispensing distal end 130 of a conventional fluid syringe 132 having a plunger assembly 134 and a fluid-containing/dispensing barrel 136. The syringe 132 can be filled with any inert, biocompatible fluid, such as normal saline. The volume of the syringe 132 is typically sufficient to fill the lumen of the catheter and the balloon 114. In use, the catheter 100 is guided into the urethra, bladder or another body cavity in which localized pressure measurement is desired. Typically, following insertion, the syringe 132 containing fluid, is applied to the proximal fitting 120. The fluid is then directed into the lumen so as to at least partially fill the balloon 114 and interconnected lumen. A proximal side port (not shown) communicating with the lumen may allow for the expulsion of air as fluid fills the catheter balloon and lumen. After a predetermined quantity of fluid is introduced to fill the space, the syringe may be removed from the fitting 120 and another syringe not shown) is applied to the fitting. The plunger of the second syringe is drawn proximally, out of the barrel to create a low-pressure vacuum at the inlet of the catheter. The vacuum allows air bubbles within the lumen and the balloon 114 to be evacuated. It is desired that all air bubbles be removed from the lumen and balloon before a pressure reading is taken. This may entail multiple cycles of filling and vacuum-application until the practitioner is fairly certain that no air bubbles remain. Due to the small diameter of the lumen, air bubbles may have a tendency to adhere to the luminal walls due to surface tension. Thus, removal of all bubbles may require several fill and vacuum-application cycles. Tapping the catheter shaft 101 to jar adhering bubbles may also be desirable. Once bubbles have been removed from the catheter 100, the proximal end fitting 120 (or another connection) is connected to a pressure transducer assembly 140. The transducer assembly includes a mating fluid fitting 142 on the end of the transducer housing 142 that is sized to mate with the catheter proximal fitting 120. Within the transducer assembly's housing, in communication with the inlet of the fitting 142, is a fluid-impermeable membrane (not shown) that communicates with an electronic transducer element. The transducer element and its associated internal electronics are electrically connected by a multi-pin connector 146 to a cable 148. The cable 148 extends a predetermined distance to an opposing connector 150 that interfaces with an appropriate electronic device 160. The electronic device 160 can include a pressure value readout 162 of appropriate scale and type, as well as other control electronics and power supply systems.

The above-described system and method for employing a pressure sensing catheter and sensing internal body pressure has several disadvantages. In particular, the practitioner must fill the catheter lumen and balloon with an appropriate level of fluid, and then ensure removal of any air bubbles. This is a time-consuming process, and may lead to inaccuracies if air bubbles remain. It may be difficult to determine whether residual air bubbles are present in the filled catheter, particularly when the catheter is already inserted into the patient. In addition, the extra time required to fill the catheter with fluid means that the patient must endure a longer procedure-particularly where the catheter is first introduced to the patient's body, and then filled with fluid. Moreover, the subsequent connection of the catheter's pressure transducer assembly makes it more likely that the system will experience air bubbles or leaks, after it is filled. All of these disadvantages lead to a more time-consuming and potentially less-accurate procedure.

Accordingly, it is desirable to provide a pressure sensing catheter, and method for using such a catheter, that avoids time-consuming and inaccuracy-producing steps. Moreover, it would be desirable to provide a catheter that reliably allows for multiple pressure readings at different locations along its length without the need of multiple balloon-filling steps to be undertaken by the practitioner. Furthermore, such a catheter should provide for easy and quick connection to conventional pressure-sensing display electronics and should allow for an infusion/flushing connection to deliver fluid to the patient from a distal location along the catheter.

SUMMARY OF THE INVENTION

This invention overcomes the disadvantages of the prior art by providing a pressure sensing catheter, and method for using the same, that eliminates the practitioners' need to fill the catheter with fluid manually prior to insertion, and thereby increases the accuracy and ease of the overall pressure-sensing procedure. The illustrative catheter includes, in its proximal end, a transducer base or housing that is permanently attached to the catheter shaft. The base includes, inserted thereinto, one or more miniaturized pressure transducer assemblies, which are in fluid communication with corresponding pressure lumens that extend down the shaft and are in communication with one or more predetermined balloons by discrete channels or ports, which provide a fluid passage between the interior space of the balloon and the corresponding pressure lumen. The integral assembly includes a predetermined, previously installed charge of fluid that extends from the transducer, through the corresponding pressure lumen and into the interior volume of the sensing balloon. The charge of fluid has been made free of any air bubbles at the point of manufacture, and is delivered fully charged, so that maximum sensing accuracy and minimum setup time are achieved.

In an illustrative embodiment, wherein multiple balloons are placed at predetermined locations along the length of the catheter shaft, each balloon can include a passage or port through the wall of the shaft that interconnects with a discrete, corresponding pressure lumen. Each pressure lumen communicates with a predetermined miniaturized transducer mounted within the proximal base. The transducers are electrically connected, by appropriate removable connectors, to an electronics and display package that provides sensed pressure readings for each balloon. A plurality of pressure lumens, balloons and connected sensor assembles can be provided (four balloons/pressure lumens/sensors in one rectal catheter example). An enlarged fluid delivery (infusion/flushing) lumen can be provided, running parallel to, and separate from, the balloon pressure lumens. An outlet port along the shaft wall at, or near, the distal end of the catheter can allow for the delivery of medicaments and other fluids via a proximal luer fitting to which a syringe or other fluid-delivery device can be attached. The catheter shaft, and/or other components thereon, can be color-coded for a particular application such as rectal, urodynamic, vaginal or urethral. The shaft can also be printed with length increments relative to the midline of the distal-most balloon (or another reference point), which show the distance that that device is inserted into the body cavity.

In various embodiments, the illustrative prefilled catheter is provided to the practitioner as a closed system with no ingress or egress of fluid to or from the pressure system, and in a sealed, sterilized, polymeric package, which is ready to be opened and used without the need to fill the pressure lumens with fluid, or otherwise perform any action—other than to insert it to the appropriate location within a patient's body and apply the appropriate electrical connectors. The catheter shaft can be surrounded with a removable, saline-filled sheath that sealably engages a distal extension formed on the surface of the over-molded transducer base, at a narrowed distal region where it engages the shaft.

In various embodiments, the catheter shaft can define one or more lumens, wherein each lumen that is interconnected with a balloon is prefilled with fluid and sealed against entry or exit of fluid therefrom. Where applicable an infusion lumen provides open fluid flow between a proximal infusion/flushing fitting and a distal port. In an embodiment, the shaft defines two prefilled pressure lumens, each interconnected with the interior space of a respective balloon located at predetermined positions along the shaft. The pressure lumens each interconnect respective pressure transducers mounted along the transducer base. An infusion/flushing lumen is also provided along the shaft. In another, single balloon embodiment, one of the two pressure lumens, while present, is sealed at each end. Alternatively only one pressure lumen is provided. In a further embodiment, the shaft is free of any infusion/flushing lumen, and the pressure lumen is centrally located along the shaft in communication with a transducer in the base and a port that resides within the interior of a single balloon—the lumen being prefilled with an appropriate level of fluid.

BRIEF DESCRIPTION OF THE DRAWINGS

The invention description below refers to the accompanying drawings, of which:

FIG. 8 is a side cross section of a pressure sensing catheter, including a fluid-infusion/flushing fitting and port according to an alternate embodiment;

FIG. 9 is a side cross section taken along line 9-9 of FIG. 8 through the midline of the catheter's pressure sensing balloon;

FIG. 18 is a side view of a pressure sensing catheter according to an further illustrative embodiment, including a single pressure sensing balloon located at predetermined position along the length of the catheter shaft near the distal end, and including a distal infusion/flushing fitting and tubing, adapted generally for urinary applications;

FIG. 19 is a more detailed partial side cross section of the pressure transducer base of the pressure sensing catheter of FIG. 18 including one pressure transducer and one sealed location normally adapted to mount a second pressure transducer;

FIG. 20 is a side view of a pressure sensing catheter according to an further illustrative embodiment, including a single lumen and interconnected pressure sensing balloon located at predetermined position along the length of the catheter shaft near the distal end, adapted generally for rectal applications;

FIG. 21 is a more detailed partial side cross section of the pressure transducer base of the pressure sensing catheter of FIG. 20 including one pressure transducer and one sealed location normally adapted to mount a second pressure transducer, and being generally free of a infusion/flushing lumen;

FIG. 22 is a cross section of the single lumen catheter shaft taken along line 22-22 of FIG. 20.

DETAILED DESCRIPTION

Figure 1:
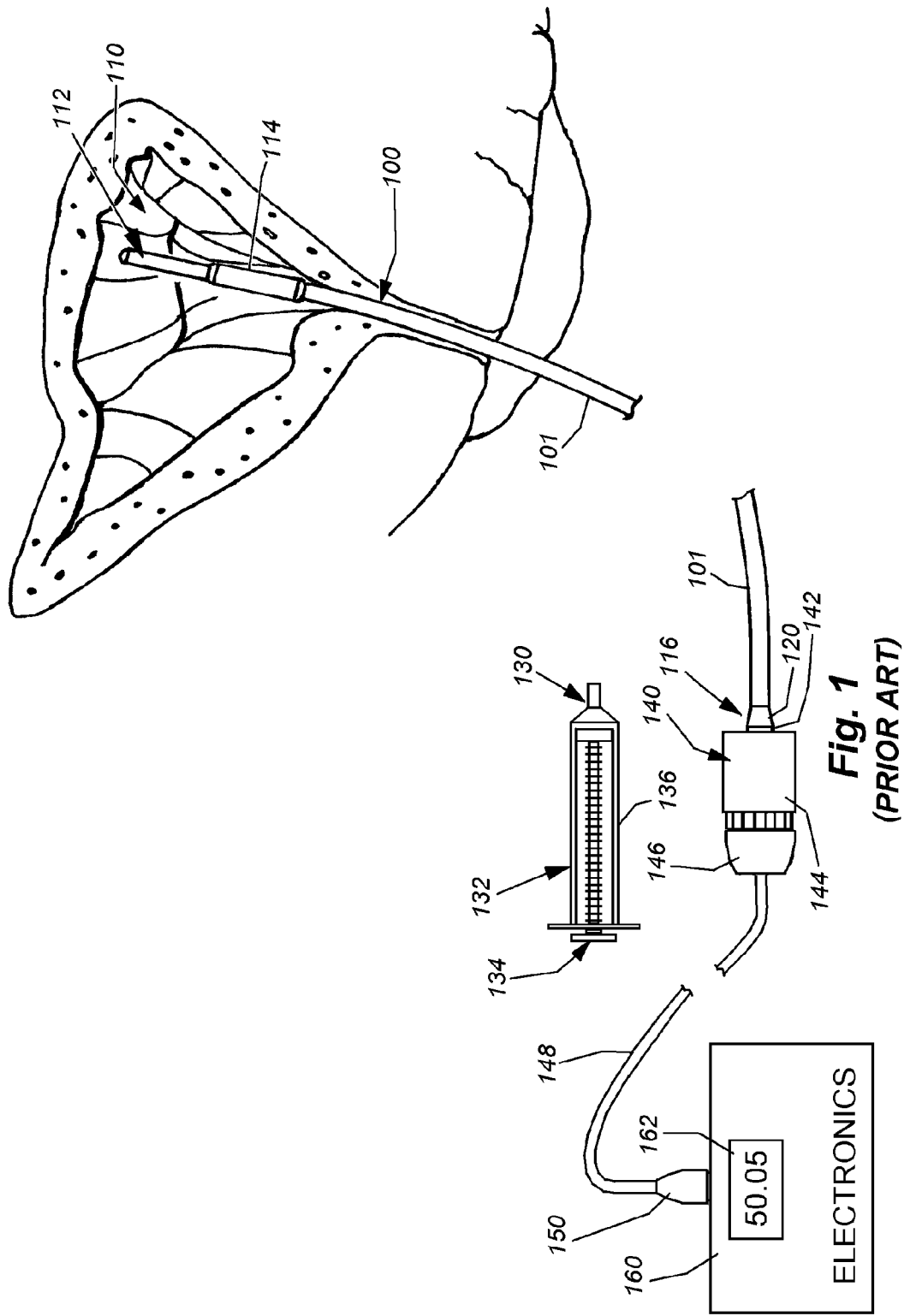
FIG. 1, already described, is a diagram of a pressure-sensing catheter system according to a prior implementation.
Figure 2:
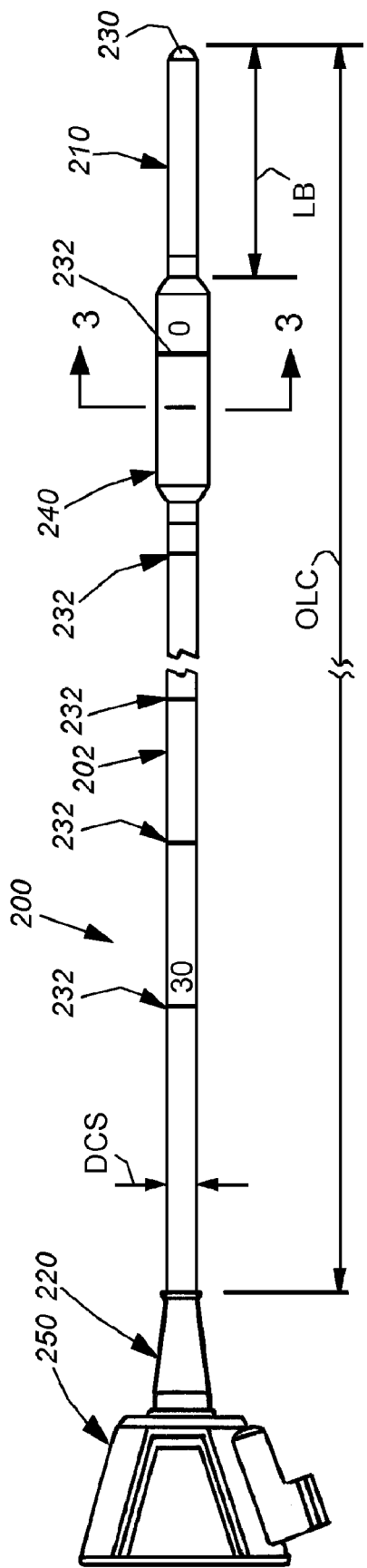
FIG. 2, is a side view of a single-balloon pressure sensing catheter according to an illustrative embodiment of this invention.

FIG. 2 shows a pressure sensing catheter 200 according to an illustrative embodiment of this invention. The catheter 200 includes a shaft 202 having a distal end 210 adapted for insertion into a body cavity of the patient and an opposing proximal end 220 that remains posterior of the patient to be accessed by the practitioner. The distal end includes a rounded over tip 230 that is sealed against moisture infiltration in this embodiment. The tip allows for easier guiding of the distal end 210 into a body cavity or other location. The catheter 200 of this example is a urodynamic catheter, and its shaft 202 has an overall length OLC of approximately 54 centimeters in one embodiment. The overall length of the shaft is highly variable to suit other applications, including rectal catheters, an example of which will also be described below. As shown, the shaft 202, which is constructed from a semi-rigid/flexible polymer to be described further below, includes a series of printed-on or fused-in distance markings 232 of a contrasting color (black, for example) with respect to that of the shaft 202. The markings 232 begin at the center line of a balloon 240 in accordance with this embodiment. The markings 232 are spaced at one-centimeter intervals for thirty centimeters. In this example, indicia (0 and 30 centimeters are shown) are provided at five centimeter intervals along the shaft. These markings assist in determining the penetration depth of the catheter's pressure sensing balloon 240. As discussed further below, the pressure sensing balloon 240 of this embodiment has a center line positioned at approximately 28 millimeters from the distal tip 230 (length LB). Again, the balloon positioning is highly variable for different types of catheters and different applications in accordance with this invention.

The proximal end 220 of the catheter 200 includes a transducer housing or base 250 in accordance with an embodiment of this invention. As will be described further below, the transducer base 250 attached by a permanent, fluid-tight seal to the proximal end 220 of the catheter 202 to prevent pressure fluid loss and external fluid infiltration. In this embodiment, the exemplary urodynamic catheter defines a 7-French-diameter catheter shaft 202. That corresponds to a diameter DCS of approximately 0.096 inch, with a tolerance of ±0.003 inch.

Figure 3:
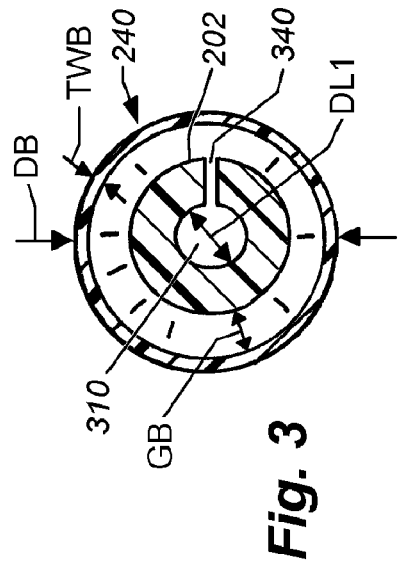
FIG. 3 is a cross-section taken along line 3-3 of FIG. 2, through the midline of the catheter's pressure sensing balloon.
Figure 4:
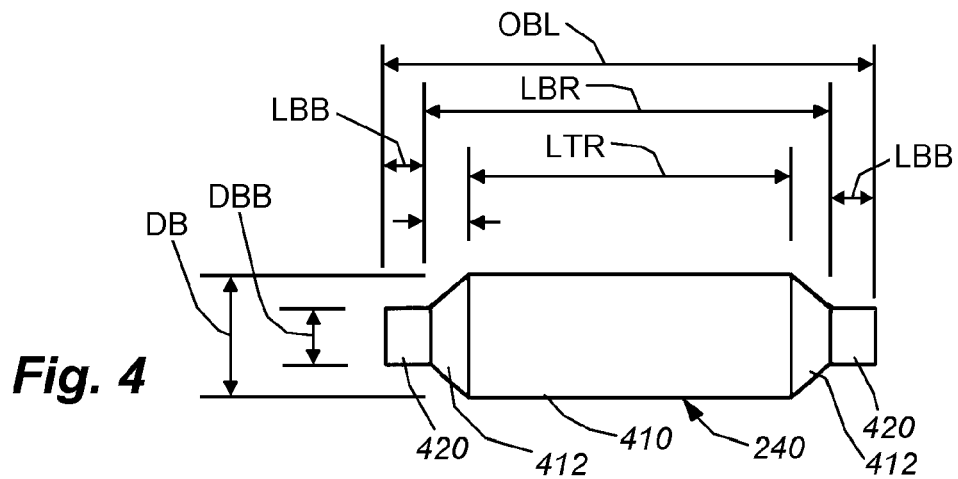
FIG. 4 is a more detailed side view of the pressure sensing balloon for use in the catheter of FIG. 2.

Reference is now made to FIGS. 3 and 4 which show, respectively the cross-section of the loom 240 with respect to the catheter shaft 202 and a more detailed side view of the balloon 240. The balloon 240 is constructed from a molded pliable elastomer that is biocompatible (FDA class VI approved, for example), and has properties that afford flexibility while avoiding buckling during insertion. The material should also be capable of extrusion formation with the requisite small-diameter lumens to be described below. In one example, the shaft elastomer material is Tecoflex 80A (polyurethane-based) available from Thermedics, Inc. of Wilmington, Mass., or an equivalent material. Like other materials used to construct the catheter 200, the balloon 240 should also be biocompatible and FDA class VI approved. The pressure sensing balloon 240 has an approximate wall thickness TWB (FIG. 3) of between approximately 0.001 and 0.005 inch. The outer diameter DB of the balloon 240 is approximately 3.0 millimeters. Thus, the gap GB between the shaft 202 outer surface and balloon inner surface is approximately one millimeter, thereby defining the fill-space for pressure working fluid within the balloon.

As shown in the cross section of FIG. 3, the catheter shaft 202 includes balloon inflation or pressure lumen 310 running along its length and terminating adjacent the balloon interior before the distal end 210. In this embodiment, the pressure lumen 310 has a diameter DL1 of approximately 0.02 inch. This luminal diameter is highly variable depending upon the corresponding outer diameter DCS of the catheter shaft and the placement of other lumens within the catheter, as will be described below. In this embodiment, the balloon 240 is a unitary structure that is adhered to the outer surface shaft using adhesives, ultrasonic welding or another technique that allows the formation of a secure, fluid-tight seal that is capable of withstanding a pressure differential equivalent to 200 centimeters of vertical water column. The balloon 240 is divided into a plurality of geometric sections when taken in side view in FIG. 4. The main barrel 410 defines a cylinder with an outer diameter DB of approximately 3.0 millimeter as described above and an overall length LBR of approximately 0.197 inch. On each end of the balloon is an inwardly tapered region 412. The tapered regions 412 have a length LTR of approximately 0.16 inch. The opposing end bases 420 have an outer diameter DBB that is approximately 0.100 inch. The inner diameter of each end base 422 is similar to the diameter DCS of the catheter shaft, and more particularly, approximately 0.097 inch. Each end base 420 has a length LBB of approximately 0.043 inch, providing an overall balloon length OBL of approximately 0.315 inch. Note that the dimensions described herein are merely exemplary of an illustrative embodiment. These dimensions can be widely varied for different sizes and applications of catheter according to alternate embodiments, some of which are described below.

Figure 5:
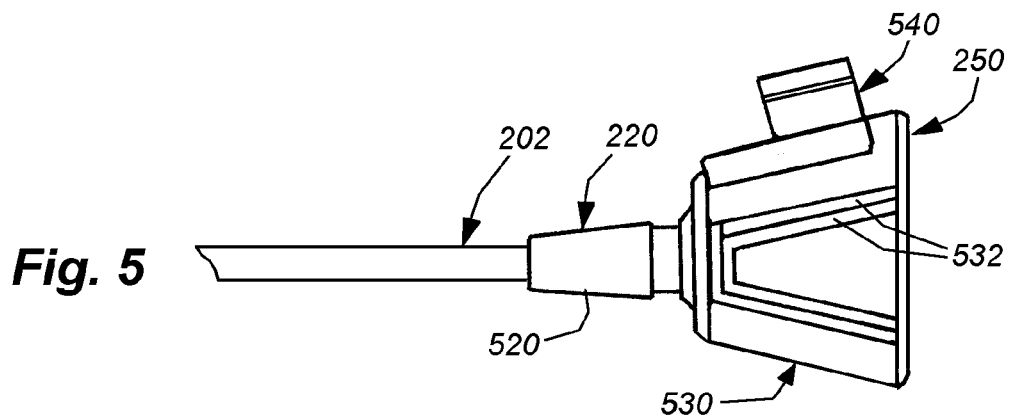
FIG. 5 is a more detailed side view of the proximal pressure transducer base for the catheter of FIG. 2.
Figure 6:
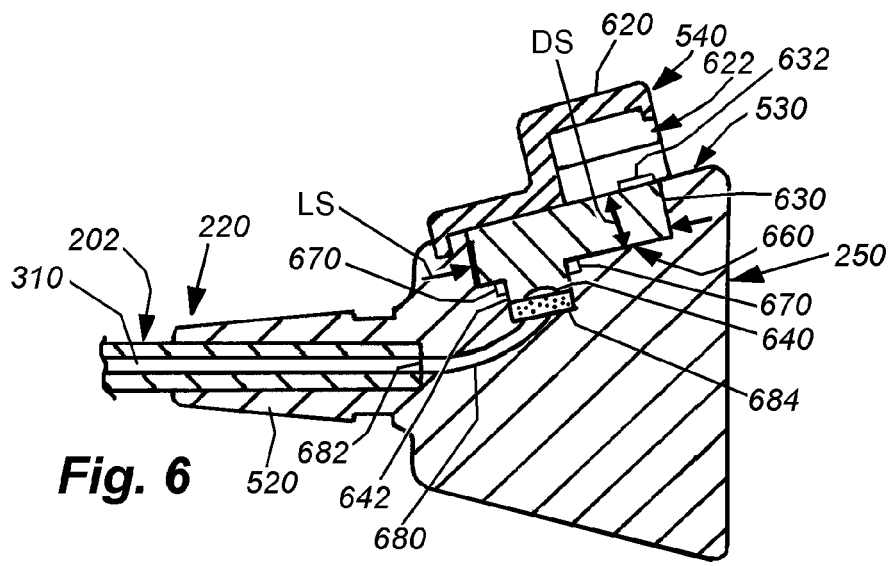
FIG. 6 is a midline side cross section of the proximal pressure transducer base of FIG. 5.

Reference is now made to the proximal end 220 of the catheter 200 as described in FIGS. 5 and 6. The outer shape of the proximal transducer base 250 is widely variable. In general, the base 250 includes a distal extension 520 that is molded unitarily with the remainder of the base. A rear transducer housing portion 530 of the base 250 tapers proximally in an outward direction and has the appearance of a wedge in this embodiment. Note that the size and shape of the base is widely variable, and at least partially an ornamental design choice. The base 250 is generally rectangular in cross section (taken through an elongated axis of the base 250 and shaft 202), and can include a stepped 532 profile. As shown, the housing portion 530 of the base 250 includes one attached sensor assembly 540 according to the depicted embodiment of this invention. The sensor assembly 540 is secured by clips or adhesives onto the underlying base 250 along a top side.

As shown in FIG. 6, the sensor assembly 540 consists of an outer cap section 620 that defines a receptacle 622 into which an appropriate electrical connector can be inserted. In this, and other embodiments described herein, the cap section can include an interface with the transducer base that acts as an integral or unitary clip. The transducer base 250 can be modified with a slot that allows for a mating engagement with the cap section 620. Thus the cap section can act as a retaining clip for the underlying sensor/pressure transducer assembly 630. The cable connector used in conjunction with the sensor assembly herein can be similar to an RJ-style telephone connector having four pins. The sensor cap 620 overlies the sensor/pressure transducer assembly 630. Note, as used herein, the term "sensor" or "sensor assembly" shall refer generally to the pressure-transducer hardware (including fluid-impermeable membrane and microelectronic pressure sensing interface) along with associated electronics needed to deliver a pressure value signal to the attached connector or other cable lead interconnected with display electronics. In the illustrative embodiments, the sensor assembly 630 includes printed circuit board contacts 632 that are exposed within the receptacle 622. Spring-loaded connector tabs (not shown) from the cable connector make electrical contact with the pads 632. The cap 620 likewise ensures that these tabs remain in pressurable contact with the contacts 632. The internal circuitry and the mechanics of the sensor have been omitted. An illustrative pressure sensor is the model MPS-200G medical pressure sensor available from Memstech Bhd. of Kuala Lumpur, Malaysia. The illustrative sensor assembly 630 has an overall length LS of approximately 10.5 millimeters and a transverse width of approximately 6 millimeters. It has a depth DS of approximately 3 millimeters. It is available in a variety of inherent impedance values, and can be employed in a variety of medical pressure-sensing applications.

The illustrative sensor assembly 630 includes a fluid-contacting membrane 640 mounted within a cylindrical housing extension 642. This housing extension 640 is generally circular having a diameter of approximately 4.8 millimeters. The attached, rectangular sensor body and cylindrical extension 642 fit within a well 660 that is molded and/or machined into the base 250. The sensor assembly 630 is secured by adhesives, clips or another acceptable mechanism into the well 660. An O-ring 670 or other sealing member is positioned between the sensor housing and the base well 660. In this manner, a fluid-tight seal is maintained between the fluid-contacting membrane 640 and the exterior of the transducer base 250.

As also shown in FIG. 6, the distal extension 520 of the transducer base 250 surrounds and seats the proximal end of the catheter shaft 202 within a socket defined by it. The shaft and base can be secured together by adhesives, welding or any other permanent-securing/sealing technique. The length of the socket formed within base's distal extension 520 is sufficient to ensure a firm bond between the base 250 and shaft 202. As shown, the pressure lumen 310 extends through the shaft and proximally into communication with a molded pressure lumen 680 that, itself, extends between the proximal end 682 of the shaft lumen 310 and the well 684 formed in the base 250 beneath the sensor membrane 640. Thus, a continuous, sealed channel extends from the sensor membrane 640, through the lumens 310, 680 to the distal balloon 240. Referring particularly to FIG. 3, the distal end of the shaft's pressure lumen 310 is vented into the interior space of the balloon 240 through a radially aligned fluid channel or port 340. This port can be drilled or otherwise cut into the sidewall of the catheter shaft and resides approximately at the balloon midline mark 232 in FIG. 2). The diameter of the pressure port 340 can vary. In an illustrative embodiment, it is approximately 0.005-0.015 inch, but the actual diameter of the pressure port is highly variable. Likewise, this and other ports provided along the catheter shaft can be ovular (or another geometry) in shape, with a major axis aligned substantially along the catheter shaft's longitudinal axis.

Figure 7:
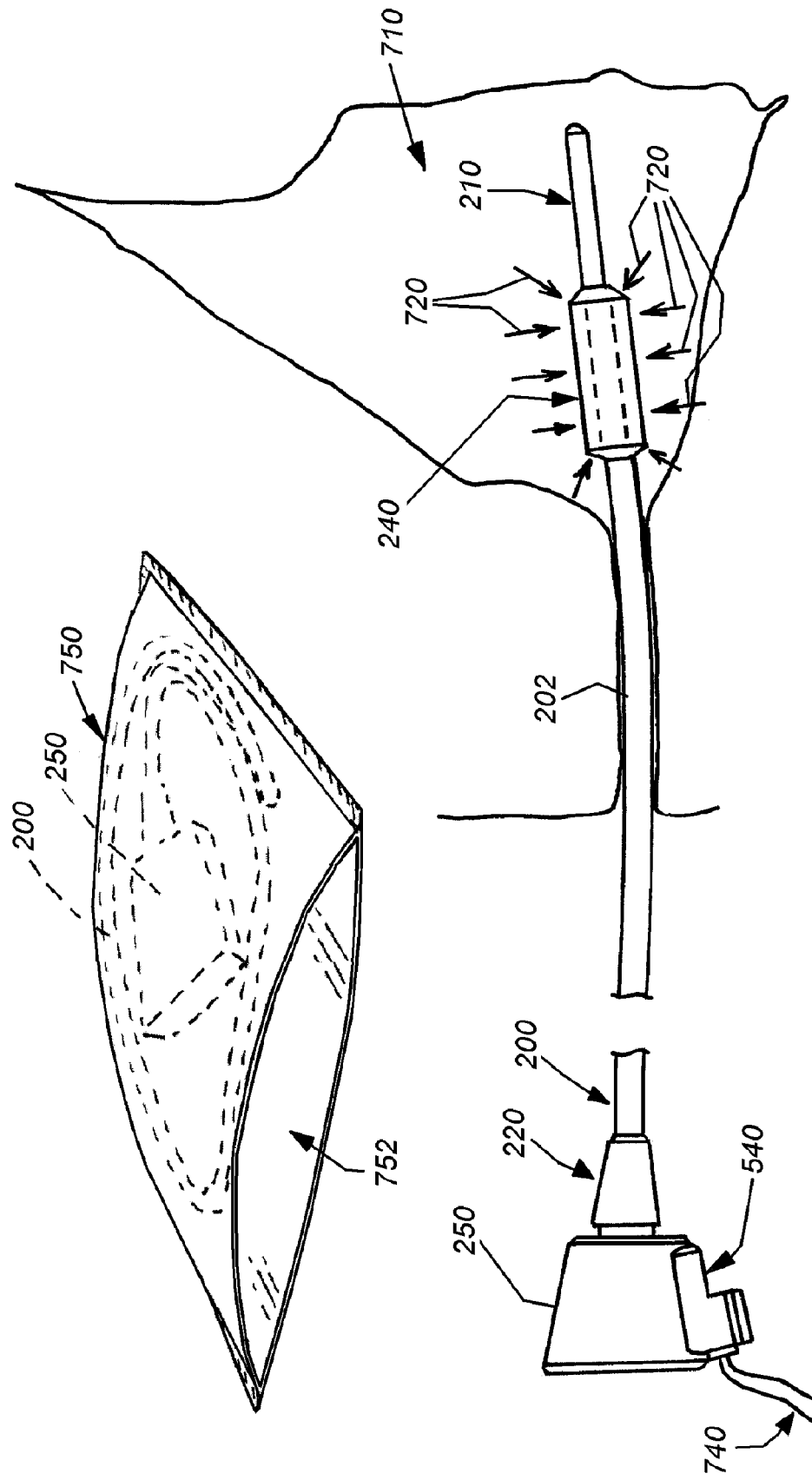
FIG. 7 is a diagram of the catheter at FIG. 2 shown inserted into an exemplary internal body location, with the body fluid pressure shown acting on the catheter sensing balloon.

In operation, as shown in FIG. 7, the catheter 200 is inserted into a body cavity and/or orifice of the patient at a location containing a fluid or surrounding tissue under pressure (for example, the bladder 710). The surrounding fluid exerts force (arrows 720) on the inserted balloon 240. This causes the fluid-filled balloon 240 and interconnected lumen 310 to respond by exerting pressure on the membrane 640 of the sealed sensor assembly 540 at the proximal base 250. The sensed pressure is converted into an appropriate electrical signal by the sensor's electronics, and is transmitted over the cable 740 to the display electronics (see below). In this illustrative example, the balloon 240 and pressure lumen 310 are prefilled with fluid and substantially free of air bubbles so that pressure applied to the balloon is accurately transmitted to the membrane. Notably, the balloon 240, shaft 202 and base 250, along with the attached sensor assembly 540 are all a sealed, integral unit, which is delivered to the practitioner in a sterile state with working fluid already loaded there into and isolated from the outside environment. As shown (in phantom), the prefilled catheter 200 (and any other catheter embodiment herein) is provided to the practitioner from the manufacturer in a sealed, sterile pouch 750. The pouch 750 is shown having been opened at one end 752 by the practitioner to remove the catheter 200. The pouch can be constructed from any acceptable material, such as Tyvek® sheet, or advantageously using a metal/metalized foil material. A foil pouch helps to further prevent the loss of fluid over time, which might occur through the relatively thin balloon wall. The pouch and catheter therein can be sterilized subsequent to sealing using a gamma ray source in accordance with conventional techniques.

Note, as used herein, the terms "prefill", "prefilled" or "prefilled charge" of fluid shall be defined as a quantity of working fluid that is contained in the lumen and balloon interior space and placed therein under manufacturing conditions (as opposed to being practitioner-filled during use) before delivery to a practitioner for use. In accordance with the definition, this prefilled charge is inserted prior to the permanent or semi-permanent securing/sealing of the communicating sensor assembly into the transducer base and into contact with the fluid. Permanent securing entails use of adhesives or clips that become inaccessible except by damaging the base. Semi-permanent securing entails use of clips or other mechanisms that are not generally user/practitioner-serviceable without damaging the assembly and/or are not readily reassembled once disassembling. Thus, as used herein, the terms "prefill", "prefilled" and the like refer to a catheter assembly that is delivered as a filled, sealed unit-in direct contrast with a practitioner-filling process where a transducer is later applied over the practitioner-filled catheter, which has been delivered to him or her as an unfilled unit. The pressure system (balloons, pressure lumens and sensors) of the illustrative catheter is, thus, provided as a closed system that is free of ingress or egress of fluid therefrom when delivered to the practitioner. Likewise, the completed base, with sensor assemblies installed can be defined as an "integral" assembly. More generally, the complete prefilled catheter can be considered an "integral" catheter assembly as not components other that electrical connectors or an infusion fluid source are attached or removed by the practitioner. As stated, this results in a more accurate, and easier to use device. Construction of this prefilled catheter assembly according to various embodiments of this invention will now be described in further detail.

In an illustrative embodiment, the shaft 202 is formed from an extrusion from an appropriate semi-rigid polymer material. This material can be any biocompatible material, such as Pellethane 2363-90A, which is used in the illustrative embodiment. In alternate embodiments, materials such as urethane and/or polyvinylchloride (where permitted by regulations) can be substituted. The balloon 240 is passed over the shaft 202 to the appropriate location where it overlies the pressure port 340 (FIG. 3) that allows fluid to pass between the pressure lumen 310 and the outer surface of the shaft 202. The balloon end bases 430 are then permanently secured to the exterior surface of the shaft 202 using welding, adhesives, or the like. In another step, occurring either before or after the attachment of the balloon 240 to the shaft 202, the proximal transducer base 250, without sensor attached, is then secured using adhesives, welding or another technique to the proximal end of the shaft 202. This attachment should ensure that a fluid-tight seal is maintained between the base 250 and the shaft 202, and that the proximal end of the pressure lumen 310 of the shaft is unobstructed and communicates freely with the molded pressure lumen 680 within the base 250. Once the balloon 240 and base 250 have been secured to the shaft and the interfaces between these parts have cures or hardened sufficiently, the balloon 240, shaft pressure lumen 310 and molded pressure lumen 680 are filled completely with a biocompatible fluid, such as normal saline. This filling process occurs in a manufacturing environment, rather than in the field by a practitioner. Thus, it can be performed by manual and/or automated techniques. In one example, a syringe or other fluid source introduces fluid under elevated (with respect to atmospheric) pressure to the well 684, driving out any air bubbles within the filled space. Through repeated cycles of filling and then applying a mild vacuum (using for example, an attached syringe with a plunger drawn outwardly), the entire space of the balloon 240 and the lumens 310, 680 is filled with fluid while all air bubbles are evacuated. The catheter assembly maybe subjected to mild vibration to further assist in dislodging any air bubbles during the filling and evacuation process. Once sufficient cycles have occurred so as to ensure complete filling of fluid, and air evacuation, the sensor well 684 is left with a small quantity of fluid. Note that, when completely filled, the balloon 240 may not appear to be fully inflated, having a slightly wrinkled appearance. However, due to the lack of air bubbles, any applied pressure on the balloon will be transmitted as a corresponding fluid pressure to the well 684 and confronting sensor membrane. Thus, having completely filled the fluid space, the sensor assembly 540 is now directed into the base well. A seal (O-ring 670) surrounds the sensor housing's cylindrical base extension 642, so that the final connection is sealed. As the sensor is seated into the well, any remaining fluid either escapes from the housing or is driven under mild pressure back into the balloon to slightly expand its shape. The resulting assembly is completely fluid filled and substantially free of air. Thus, it ensures an accurate pressure reading that is reliable and repeatable in each catheter delivered to a practitioner. The sensor assembly, once seated, is secured to the base 250 using a spring clip, adhesive or another desired technique.

In alternate embodiments, the pressure sensing catheter of this invention can be provided with a shaft having additional lumens that enable the use of additional or remotely positioned balloons and/or fluid infusions/flushing channels. Reference is now made to the embodiment of FIGS. 8 and 9. In this embodiment, the illustrative catheter 800 includes a shaft 802 with an associated distal end 810 and proximal end 820. The catheter 800 includes a base 850 at its proximal end and a balloon 840 at its distal end. The balloon 840 is similar in size, shape and materials to the above-described balloon 240 of FIG. 206. That is, it is secured in a fluid-type arrangement to the outer surface of the catheter shaft 802. The outer diameter DCS1 of the catheter shaft 802 is also similar to the diameter DCS described above (approximately 0.096 inch). The outer diameter DB1 of the sensing balloon is also similar in diameter to the diameter DB of the balloon 240 described above. In the depicted urodynamic catheter embodiment, the diameter DB1 is, thus, approximately 3.0 millimeters. The transducer base 850 includes a sensor assembly 852 that is similar in size, shape and performance to the sensor assembly 540 described above. The illustrative base 850 differs in that it allows for the mounting of an infusion/flushing lumen with an external connection tube 870. This connection 870 includes a proximal end connector 872 of conventional design that is arranged to receive a conventional syringe or other fluid-infusion device. The overall length of the connection tube 870 can be approximately 20 centimeters in an illustrative embodiment. The length of this tube 870 and its proximal connector fitting 872 is highly variable in alternate embodiments.

Figure 10:
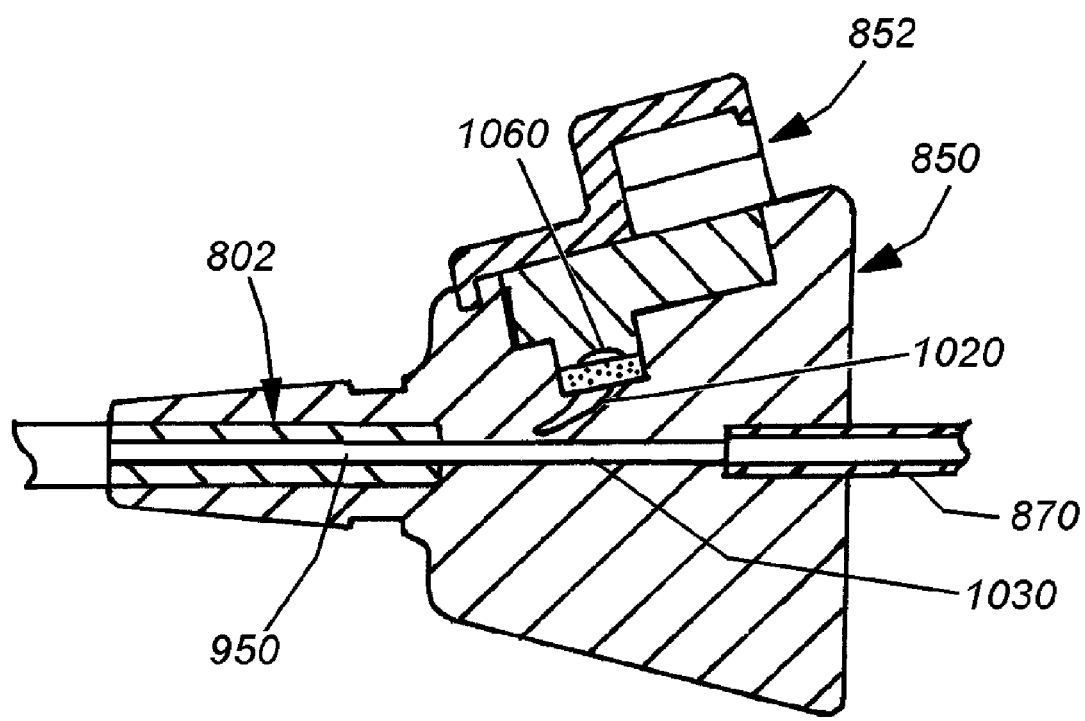
FIG. 10 is a midline side cross section of the pressure transducer base of the pressure sensing catheter of FIG. 8.

As shown in the cross section of FIG. 9, taken through the balloon 840 at or near its midline, the catheter shaft 802 defines two discrete lumens. The pressure lumen 910 is shown offset from, and parallel to, the central longitudinal axis 920 of the shaft 802. A radial channel or port 930 allows fluid to pass from within the space 932 defined between the inner surface of the balloon 840 and the outer surface of the shaft 802. Thus, as described above, any external pressure applied to the fluid in the balloon's interior space 932 exerts pressure through the port into the lumen 910 and back to the sensor 852. A second lumen 950 of larger diameter is also provided within the shaft 802. This lumen 950 is also offset from, and parallel, to the central, longitudinal axis 920 of the shaft. The larger lumen 950 defines a conduit for delivering infusion and/or flushing fluids trough the shaft 802. The infusion/flushing lumen 950 has an approximate diameter DFL of 0.042 inch in the illustrative embodiment. This diameter is highly variable. The corresponding inflation/pressure lumen 910 has a diameter DPL1 of approximately 0.02 inches. In this embodiment, the infusion/flushing lumen 950 is connected through a radial channel or port 952 (shown in phantom) to a distally located outlet port 880 (FIG. 8) positioned along the side of the catheter shaft near the distal end 810. In one embodiment the outlet port 880 is proximally set back approximately 13 millimeters from the distal tip. However, the placement of the infusion/flushing port on the shaft 802 is also highly variable. The outlet port 880 and adjacent channel 952 each have a diameter of approximately 0.03 inch in the illustrative embodiment. As shown in FIG. 10, the base 850 includes a molded pressure lumen section 1020 that passes into the catheter shaft 802. Thus, it is only partially shown as it extends outside the depicted midline cross section through the base 850. A corresponding molded infusion/flushing lumen 1030 is formed through the midline center of the base 850. It passes into the inflation lumen 950 of the catheter shaft. The connection 870 interconnects the proximal end of the molded infusion lumen 1030. The arrangement of lumens in the shaft 802, and their associated interconnections in the base 850, allows for fluid to communicate between the balloon 840 and the sensor membrane 1060, and also for introduced fluid to be directed down the lumen 950 and expelled from the port 880 at the distal end of the catheter.

Figure 11:
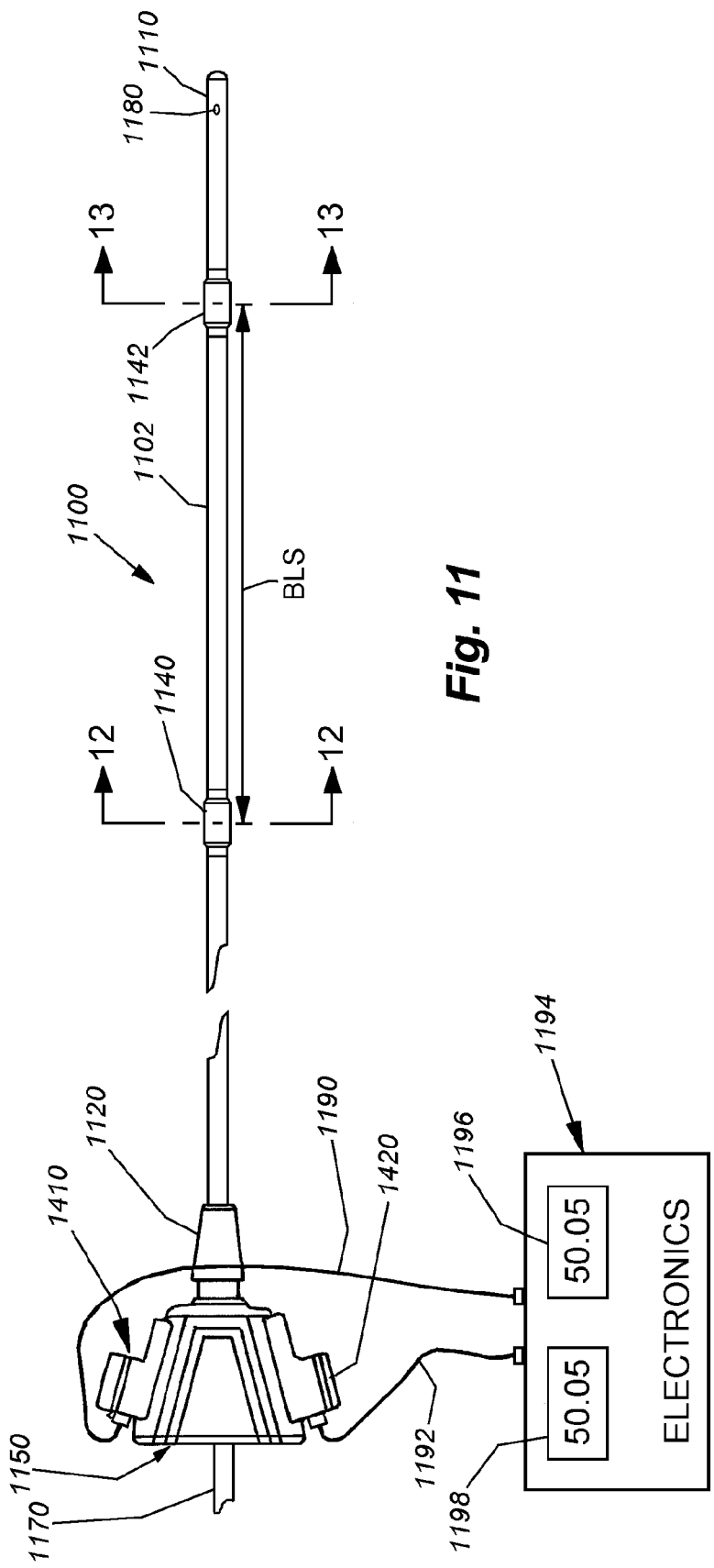
FIG. 11 is a side view of a pressure sensing catheter according to an alternate embodiment including two discrete pressure sensing balloons located at predetermined positions along the length of the catheter shaft near the distal end, and including a fluid-infusion/flushing fitting and port.
Figure 12:
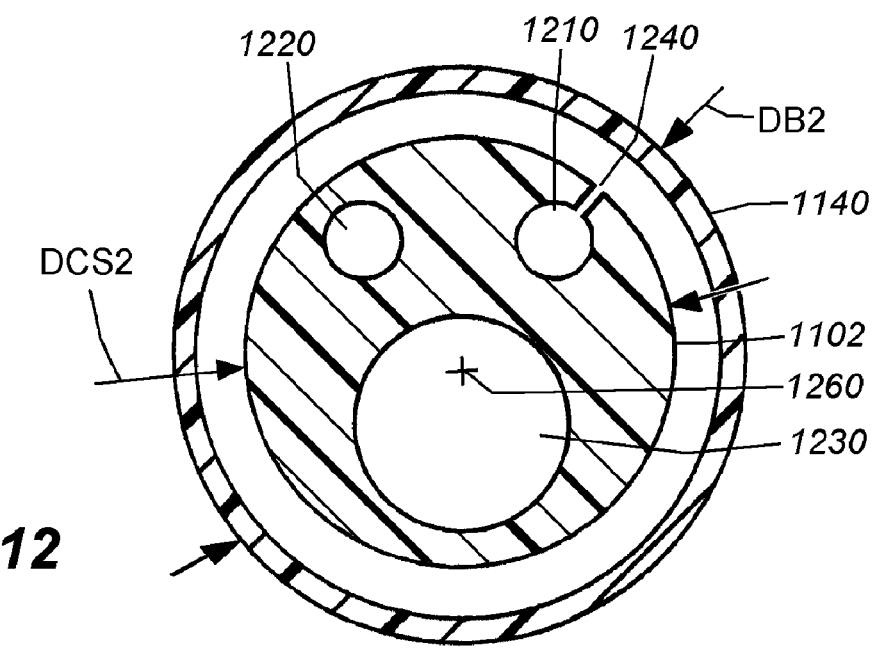
FIG. 12 is a cross section taken through line 12-12 of FIG. 11 at the midline location of the more-proximal pressure sensing balloon.
Figure 13:
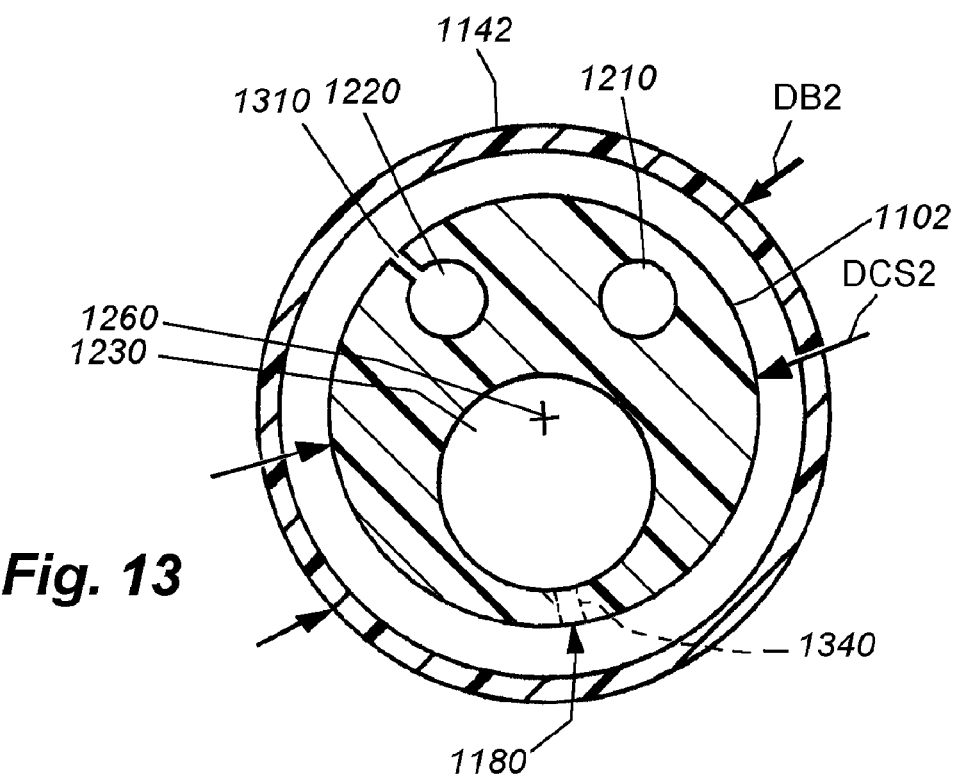
FIG. 13 is a cross section taken through line 13-13 of FIG. 11 at the midline of the more-distal pressure sensing balloon.

A further embodiment of a pressure sensing catheter according to an illustrative embodiment is shown in FIGS. 11-15. The illustrative catheter 1100 includes a catheter shaft 1102 having two pressure-sensing balloons 1140 and 1142 located along the shaft in a spaced-apart orientation with respect to the distal end 1110. At the proximal end of the shaft 1120, there is a permanently mounted transducer base 1150 that includes an infusion/flushing connection tube 1170 as described above. The infusion/flushing interconnection 1170 can include, at its proximal end, an appropriate luer fitting (see fitting 1572 in FIG. 15). In this embodiment, each balloon 1140 and 1142 senses a discrete pressure at its particular location along the shaft 1102. The spacing BLS between balloons is highly variable. In one example, the balloons are spaced apart by a distance of approximately 60 millimeters—with the midline of the more-distal balloon 1142 offset approximately 13 millimeters from the distal tip. The size of each individual balloon 1140 and 1142 is highly variable as its diameter. In one embodiment, the balloons are sized the same as the single balloon 240 described above. At least one infusion/flushing port 1180 is provided near the distal end of the catheter. This port can also have a diameter of approximately 0.03 inch. Additional flushing ports can be provided at any location along the shaft, so long as they maintain communication with the flushing lumen, the arrangement of which will be described in further detail. With reference particularly to FIGS. 12 and 13, the shaft 1102 is shown in cross section with respect to the center line of each balloon 1140 and 1142 respectably. The diameter DCS2 of the catheter shaft is the same as that described above for the other catheters (approximately 0.096 inch). Likewise, the outer diameter of each balloon DB2 is approximately the same as the other balloons described above (3.0 millimeters). There are three discrete lumens defined within the shaft. These include a first pressure lumen 1210, a second pressure lumen 1220 and an infusion/flushing lumen 1230. As shown, each lumen has its own channel or port to serve a particular function. The lumen 1210 includes the port 1240 depicted in FIG. 12. This channel provides a connecting pressure conduit for the balloon 1140. The two other lumens 1230 and 1220 pass through this location with no outlet into the interior space of the balloon 1140. Similarly, the pressure lumen 1220 has a channel or port 1310 to connect the interior space of the balloon 1132. The opposing pressure lumen 1210 is sealed at this location. Likewise, the infusion/flushing lumen 1230 is not ported into either balloon's space but rather at the more-distal port 1180. The connecting channel 1340 for the infusion/flushing port 1180 is shown in phantom in the cross section of FIG. 13. While the lumens 1210, 1220 and 1230 can be arranged in the cross section in a variety of ways, the illustrative embodiment positions each of the pressure lumens offset above (in the reference of the FIGS. 12 and 13) and transversely, at opposing sides of the central longitudinal axis. The larger, infusion/flushing lumen 1230 is centered transversely and offset below the central axis 1260. The placement of lumens should enable the catheter (and others contemplated herein) to be constructed using conventional polymer-extrusion techniques. Likewise, the walls between lumens and between the lumens and the outer surface of the shaft should be sufficiently thick and regular along the length of the shaft so that there is no risk of a wall breech, which would cause fluid to escape from the shaft or migrate between adjacent lumens.

Figure 14:
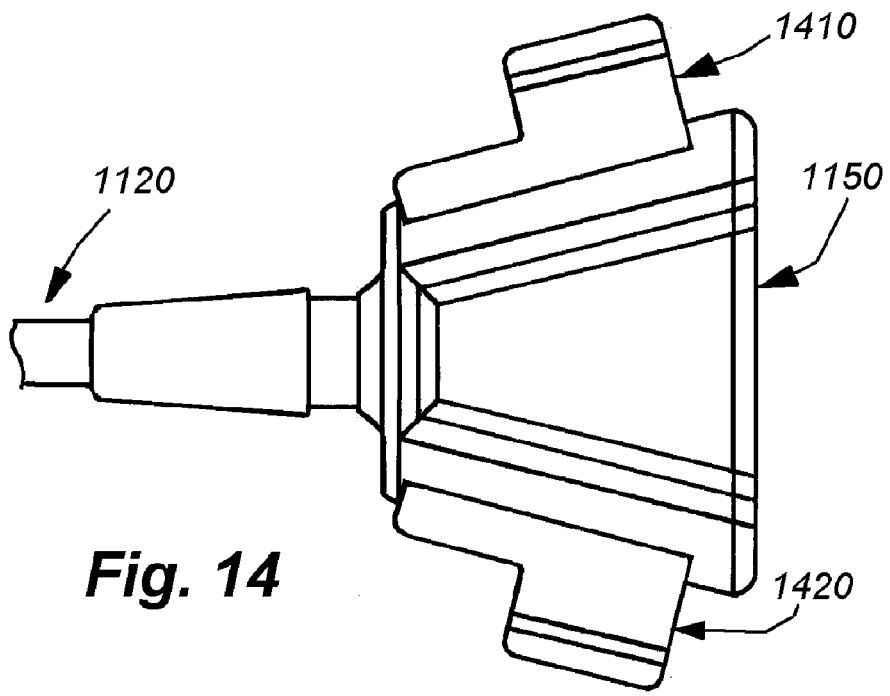
FIG. 14 is a more detailed side view of the pressure transducer base of the catheter FIG. 11.

Referring to FIG. 14, the transducer base 1150 in this embodiment includes a pair of opposed sensor assemblies 1410 and 1420. As also shown in FIG. 11, each sensor assembly is connected by an appropriate electrical cable 1190 and 1192, respectively, to a display and electronics package 1194, which includes two display readings 1196 and 1198 (one for each respective balloon 1140, 1142). The arrangement of the electronics and display package is highly variable. In alternate embodiments, a single display can show both pressure readings either as concurrently displayed data or as selectively displayed data. Each display 1196 and 1198 shows the pressure of a discrete balloon 1140 and 1142. Thus, the catheter 1100 of this embodiment allows for the sensing and display of at least two remote pressure readings within the patient's body. In this manner, one pressure reading can be from a balloon located within the bladder, while a second pressure reading can be from a balloon placed within a portion of the urethra.

Figure 15:
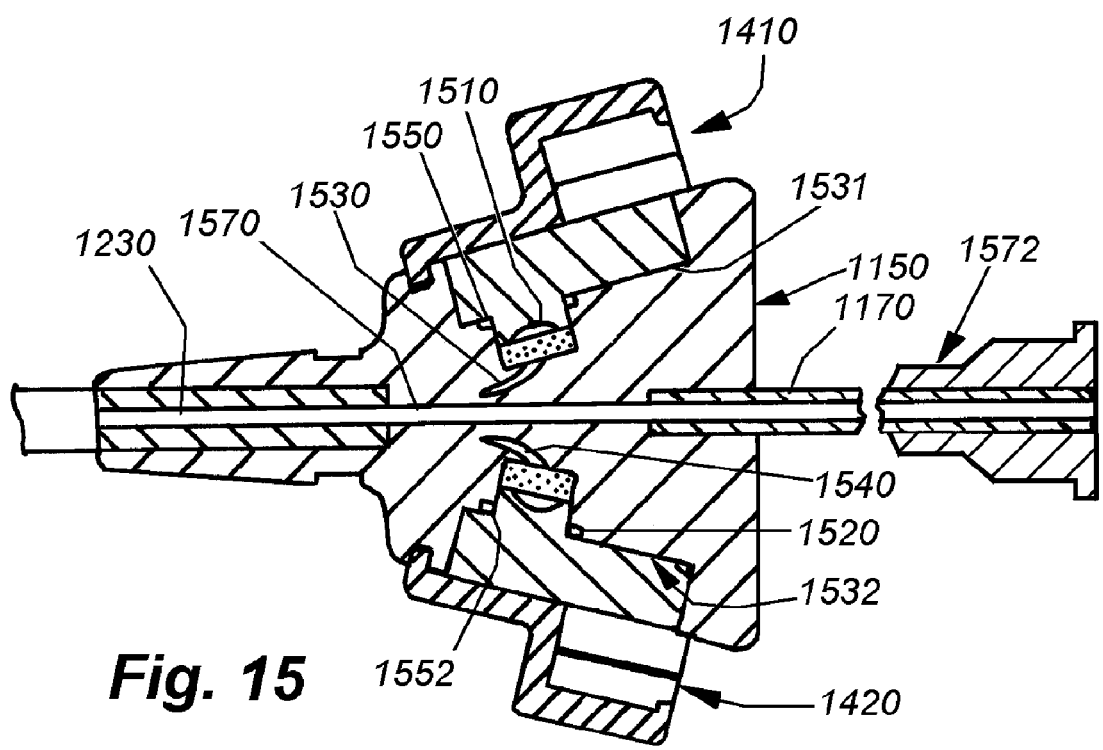
FIG. 15 is a midline side cross section of the pressure transducer base of FIG. 14, showing the interconnection of each discrete pressure transducer assembly and the fluid-infusion/flushing fitting with respective lumens that extend into and through the catheter shaft.

As shown further in FIG. 15, each sensor assembly 1410 and 1420 includes a respective sensing membrane 1510 and 1520. The membranes 1510 and 1520 are in fluid communication with respective molded pressure lumens 1530 and 1540. The sensor assemblies 1410 and 1420 are, in general, secured into the opposing sides of the base 1150 using techniques described above appropriate for a single balloon and associated sensor assembly. That is, each side of the base includes a corresponding well 1531 and 1532 for receiving the respective sensor assembly 1410 and 1420. In the depicted midline cross section of the transducer base 1150, the molded pressure lumens 1530 and 1540 are only partially shown. This is because they are located at offset orientations with respect to the distal end of the base 1150 and catheter shaft's central longitudinal axis 1260 (see FIGS. 12 and 13). Likewise, the central infusion/flushing lumen 1230 defines a molded, interconnecting section 1570 that extends through the base along the midline (offset slightly beneath the axis 1260), and communicates with the attached a proximal infusion connection 1170. As described above, the connection tube 1170 terminates at a proximal luer fitting 1572.

More particularly stated, each sensor assembly 1410 and 1420 thus communicates with a predetermined pressure lumen 1210 and 1220. That, in turn, communicates with a predetermined balloon 1140 and 1142. In this manner, each balloon delivers an independent and isolated pressure value to its respective sensor assembly. Both lumens are filled and made free of any air bubbles in a manufacturing environment according to the cyclical filling/evacuation process described above. Once each pressure lumen is filled, each sensor assembly 1410, 1420 is independently secured to the finished, filled catheter 1100 in its corresponding well 1531, 1532, and sealed with a corresponding sealing ring 1550, 1552. The completed assembly can then be sealed in a sterile package (the sealed pouch 750 of FIG. 7, for example), and delivered to a practitioner ready for use. Use of the catheter 1100 entails the attachment of the desired electrical connectors to each sensor assembly, and inserting the catheter into the patient so that it is located at the appropriate internal position. Flushing and infusion of fluids within the patient's body can be accomplished by attaching an appropriate fluid source to the fitting 1572 and expelling fluid through the port 1180. As noted above, a variety of ports can be located in communication with the infusion lumen 1230 to enable flushing to various locations along the length of the catheter shaft 1102.

As discussed above, the catheter in accordance with the various embodiments of this invention can be constructed in a variety of sizes to perform pressure-sensing functions in different regions of the body. In a rectal embodiment the catheter, the balloon dimensions, for example, are typically larger. In one embodiment of the rectal version, the balloon overall length (e.g. dimension OBL in FIG. 4) is approximately 18 millimeters, and a balloon outer diameter (e.g. dimension DB in FIG. 4) of 4.5 millimeters. The shaft may be larger in diameter, and the infusion/flushing port may allow for increased flow-through based upon a larger luminal diameter. More particularly, the number of balloons located along the length is highly variable. In a rectal embodiment of the catheter, the shaft can be adapted to provide four discrete pressure lumens located around a centralized infusion/flushing lumen (such flushing lumen being optionally omitted in alternate embodiments. In the case of four discrete pressure lumens, four corresponding pressure sensors can be provided on various surfaces/mounting locations of the proximal transducer base. The base includes appropriate molded lumens and wells to allow communication between the balloons and the sensors in a manner consistent with the teachings of this invention. Likewise, the dimensions of various elements of the catheter may be decreased in, for example, the case of a pediatric version of the urodynamic catheter. In such a pediatric example, the shaft can be sized for a 5 French diameter.

The above-described embodiments are exemplary of the catheter system according to the teachings of this invention. FIGS. 16-23 detail further illustrative embodiments that employ the teaching of this invention. In general, the structure and structure of these embodiments is similar or identical to that of the above-described exemplary versions of the pressure sensing catheter with certain modifications that will now be described in further detail.

Figure 16:
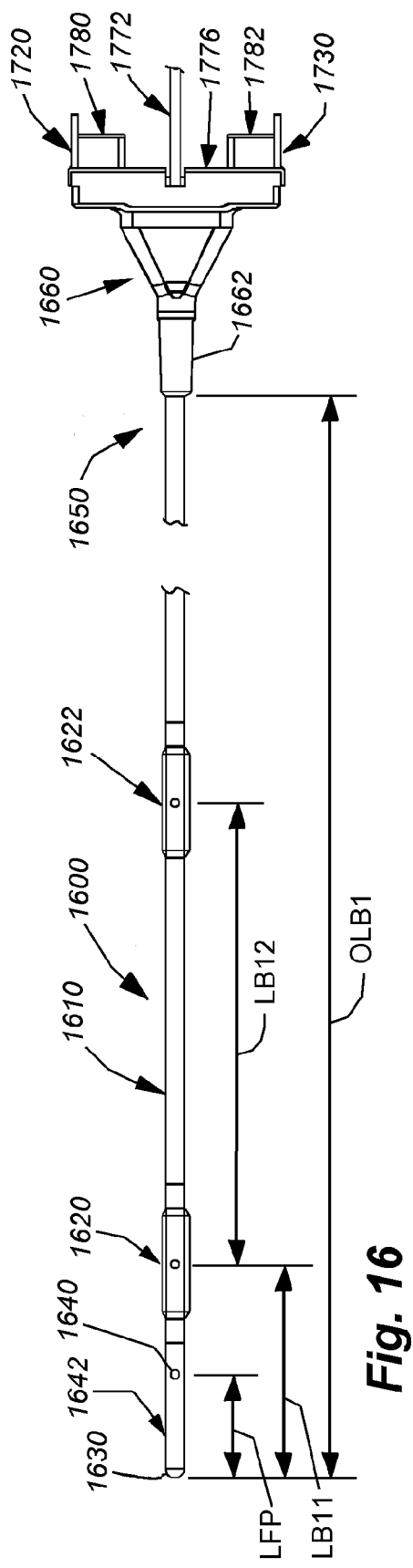
FIG. 16 is a side view of a pressure sensing catheter according to an further illustrative embodiment, including two discrete pressure sensing balloons located at predetermined positions along the length of the catheter shaft near the distal end, adapted generally for urinary applications.

With reference to FIG. 16, the pressure sensing catheter 1600 according to this embodiment includes a multi-lumen shaft 1610 similar in cross section to that shown in FIG. 12. While this design can be adapted to a variety of applications, it is typically employed for urethral/urinary applications. Each of two smaller-diameter lumens (see 1210, 1220) are in fluid communication with respective balloons 1620 and 1622, that are mounted along the exterior surface of the shaft 1610 as described generally above. The balloons 1620 define an on-center axial spacing of LB12 of approximately 57 to 63 millimeters in an illustrative embodiment. Note that recited all dimensions are exemplary, and can be varied to suit the needs of the particular application. In general, the diameter of the shaft and associated lumens can be similar or identical to the dimensions (e.g. DCS2, DPL1, DFL) of the above-described embodiments. The distal-most balloon 1620 is spaced, on-center from the sealed distal tip 1630 by a spacing LB11 of approximately 25-31 millimeters. A third larger diameter lumen (such as 1230 shown in FIG. 12 is in fluid communication with a side port 1640 near the distal end 1642 of the shaft 1610. In this embodiment the port 1640 is used for fluid flushing and/or infusion and is spaced by a distance LFP of approximately 11 to 15 millimeters relative to the distal tip 1630. The proximal end 1650 of the shaft 1610 is secured to an overmolded proximal transducer base 1660 according to an illustrative embodiment. In this implementation, the shaft's overall length OLB1 between the tip 1630 and the distal end of the base extension 1662 is approximately 530 to 545 millimeters.

Figure 17:
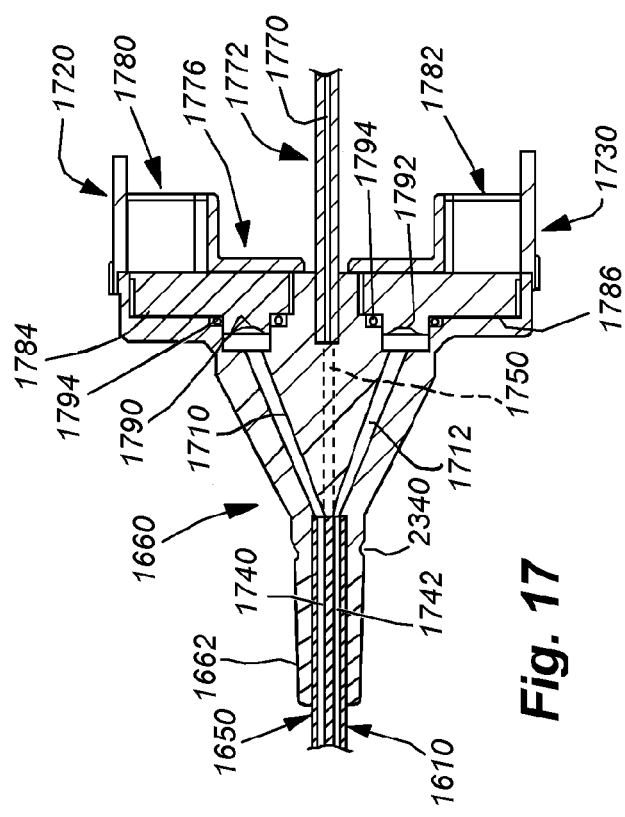
FIG. 17 is a more detailed partial side cross section of the pressure transducer base of the pressure sensing catheter of FIG. 16 including two discrete pressure transducers thereon.

The fluid-tight interconnection between the transducer base 1660 and the catheter shaft 1610 is shown in further detail in FIG. 17. Notably, the shaft 1610 extends into the base extension or stem 1662 as shown. In an embodiment, the two components are formed by overmolding the base 1660 onto the shaft 1610. In alternate embodiments, the proximal end shaft can be secured to the base by adhesives, overmolding, welding and/or various mechanical interconnections. The proximal-most end of the shaft abuts the channels 1710 and 1712, which each direct fluid to each of a pair of pressure transducers 1720 and 1730, respectively. As shown, the smaller-diameter pressure lumens 1740 and 1742 are in respective fluid-interconnection with the channels or lumens 1710, 1712. The larger diameter infusion/flushing lumen (not shown due to its offset in the cross section) interconnects with a central base channel or lumen 1750 (shown in phantom). This channel 1750 interconnects with the lumen 1770 of a proximally directed external infusion/flushing tube 1772 and fitting 1820 (see FIG. 18). The base channels/lumens 1710, 1712, 1750 can be formed in the base during molding or by another process.

In the depicted embodiment, each transducer 1720, 1730 is mounted along the proximal face of the base 1660 so as to define an overall shape that tapers outwardly into the flattened proximal base end 1776 as shown. Each transducer 1720, 1730 includes a respective socket or connector 1780, 1782 adapted to interconnect with a pressure-sensing electronics package as described generally above. Each transducer 1720, 1730 is fixedly mounted in a well 1784, 1786 located on each of opposing sides of the perpendicularly (to the shaft axis) oriented base proximal end 1776. The transducers are secured by clips, pins, adhesives or any other acceptable interconnection mechanism during catheter manufacture and after the lumens balloons and associated channels are filled and evacuated of air bubbles (as described above).

As also described above, each of the illustrative transducers includes a respective sensor membrane 1790, 1792 that confronts a respective channel 1710, 1712. An associated O-ring 1794 seals the interconnection and prevents fluid leakage at the interface of each transducer with the transducer base 1660 once the system is assembled.

In a further embodiments shown in FIGS. 18 and 19, the catheter and transducer base structure 1800 of the embodiment of FIGS. 16 and 17 can be adapted for use in a single-balloon urinary (or other application) catheter without altering the general structure of the device. Thus, similar or identical components to those of the embodiment of FIGS. 16-17 have been provided with like reference numbers, and are not further described. In particular, the shaft 1610 is still provided within two pressure lumens 1740 and 1742. However, the interconnected channel 1712 in the base 1660 leads to either an open socket 1786 or a space-filler 1920. The pressure lumen 1742 is left free of any side port where the above-described more-proximal balloon 1622 would otherwise reside. Thus, the pressure lumen 1742, while present in the design for uniformity in manufacturing, is unused. Pressure lumen 1740 is interconnected with the channel 1710 and the transducer 1720 so as to sense pressure measurements from the more-distal balloon 1620 as described above. The fluid circuit is prefilled and evacuated as described generally above Thus a minor alteration in the design of FIGS. 16-17 can yield a single balloon pressure sensing (urinary) catheter. As shown, the external infusion/flushing tube 1772 is provided, including the end Luer fitting 1820 of conventional design. The illustrative length LPF of the tube/fitting assembly is approximately 195-205 millimeters. The length LPF is highly variable, and the fitting can be alternatively provided directly on the proximal face of the base 1660.

Note, in alternate embodiments it is expressly contemplated that the infusion/flushing lumen can be omitted from the design of FIGS. 16-19 and/or the infusion/flushing side port 1640 can be located at a differing position along the shaft. Likewise, a single pressure lumen can be provided in alternate embodiments, rather than the inactive second pressure lumen 1742. Similarly, the single balloon can be located at another position along the shaft to sense associated pressure at a different position within the body cavity. Likewise, the base can be modified to omit the channel and/or socket for the unused transducer.

FIGS. 20-22 detail a pressure sensing catheter assembly 2000 according to a further alternate embodiment. This arrangement is particularly suitable for rectal pressure-sensing applications (as well as other applications), and contains a single balloon 2020 along its shaft 2010. The catheter is free of any flushing/inflation lumen in this embodiment. Thus, the base 1660 (as described above) omits the infusion/flushing fitting, or includes a disconnected infusion/flushing fitting end 2120, that does not extend to the catheter shaft 2010. The shaft is shown with external length gradations as described above. Any of the shafts herein can be provided with such indicia. The channel 1712 and socket 1786 are disconnected from the shaft 2010. Conversely, the channel 1710 is interconnected, and in fluid communication with the proximal end of the single pressure lumen 2130, also shown in cross section in FIG. 22. The pressure lumen in this embodiment is located at or near the central axis 2220 of the shaft 2010. The diameter of the lumen 2130 is highly variable. The diameter can be approximately the same as that of the pressure lumens described above, or slightly larger. The centralization of the lumen affords the shaft 2010 a greater wall thickness. Also, by locating the lumen 2130 at, or near, the center, the catheter shaft is approximately equally flexible in all directions about the axis 2220. The proximal end of the lumen 2130 should be shaped so as to communicate with the channel 1710 or the other channel 1712 can be sealed so that the proximal end of the lumen 2130 only communicates with the active channel 1710. The system is prefilled and evacuated as described above so that pressure from the distal balloon 2020 is transmitted to the transducer 1720. The location of the balloon and other shaft dimensions are similar to those described above for the urethral catheter embodiments. In alternate embodiments, the location of the balloon(s) and other dimensions can be varied as appropriate to the application.

Figure 23:
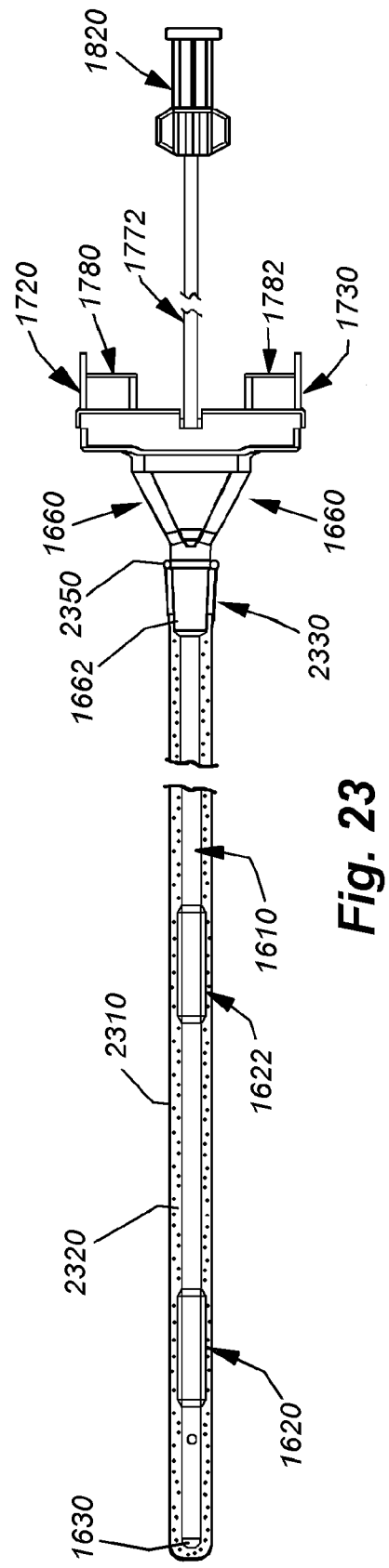
FIG. 23 is an exposed side cross section of an exemplary catheter according to an embodiment herein including a saline-filled, removable sheath for covering the catheter shaft and equalizing hydrostatic pressure with respect to the balloon(s) during shipment and storage.

In order to (optionally) protect the fluid-filled balloons during shipment and storage, a flexible polymer sleeve is filled with sterile solution (saline, for example) and surrounds the shaft. FIG. 23 depicts the above described catheter 1600 by way of example, although the sleeve 2310 can be adapted to any embodiment contemplated herein. As shown, the sleeve 2310 encases a layer 2320 of saline that cushions and provides back pressure against the balloons 1620, 1622. Thus, this arrangement helps to avoid a bursting of a balloon due to excessive external pressure applied thereto. It also prevents loss of fluid through the thin balloon membrane by osmosis. The sleeve can be constructed from any acceptable low vapor transmitting polymer, such as polyethylene or polypropylene. It includes a proximal end 2330 with a proximally outward taper that conforms generally to a distally inward taper on the base extension 1662. The sleeve end 2330 can thereby seal against the extension 1662. The taper angle can be highly variable. In an embodiment, it is approximately 0.5-3 degrees with respect to a line parallel to the shaft axis. An annular ring 2340 is formed on the extension 1662. This ring can mate with a flexible sealing lip 2350 on the sleeve end 2330 in various embodiments. In other embodiments, the sleeve end 2330 can be secured to the extension 1662 by a simple friction fit, or by an alternate securing and sealing mechanism (e.g. threaded connections, snaps, etc.). The catheter and sleeve assembly can be packaged in a rolled form in a bag, such as shown in FIG. 7, or in an elongated pouch where coiling of the unit is undesirable.

As described above, a variety of materials can be used to construct the catheter shaft and/or base. In an illustrative embodiment, an exemplary material is 65D Pellethane™ 2363 available from Dow Chemical Company of Midland, Mich. The shaft can be formed by extrusion and the base can be formed by molding or and/or machining.

It should be clear that the illustrative embodiments provide a highly useful and novel device in which the practitioner's setup time is substantially reduced by the accurate prefilling of the catheter (having one or multiple sensing balloons), and the accuracy of the sensing of internal bodily fluid pressure is substantially enhanced.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, additional pressure lumens can be provided within the catheter shaft to enable the provision of further communicating balloons. Likewise, the base can be adapted to mount additional pressure sensors and communications with those lumens. The positioning of the pressure sensors on the base is highly variable. In addition, a multiplicity of infusion/flushing ports and lumens can be provided to the catheters. These ports can be connected to independent external connections so that a plurality of fluids can be infused into the patient at different location along the catheter shaft. Accordingly, this description is meant to be taken only by way of example, and not to otherwise limit the scope of this invention.

What is claimed is:

1. A pressure sensing catheter comprising:
a catheter shaft having a proximal end and a distal end, and a first pressure sensing lumen;
a first pressure sensing balloon located on the catheter shaft near to the distal end of the catheter shaft, the first pressure sensing balloon being sealed to the shaft so as to define a fluid-tight interior space;
a transducer base forming a fluid-tight seal to the proximal end of the catheter shaft, the transducer base including a first well that receives a first pressure sensor assembly therein, the first sensor assembly including a first electrical connection to deliver a first pressure signal to a display and a first sensor membrane in fluid communication with the first pressure sensing lumen that extends from the first sensor membrane through the catheter shaft to a channel through the catheter shaft and into the fluid-tight interior space of the first pressure sensing balloon; and
wherein the first sensor assembly is secured in the first well so as to maintain a fluid-tight seal between the first pressure lumen and the first sensor membrane and wherein the first pressure lumen and the fluid-tight interior space of the first pressure-sensing balloon form a passive closed pressure system including a first prefilled charge of fluid therein.

2. The pressure sensing catheter as set forth in claim 1 further comprising,
a second pressure sensing balloon located on the catheter shaft near to the distal end and spaced-apart therealong from the first pressure sensing balloon, the second pressure sensing balloon being sealed to the catheter shaft so as to define a fluid-tight interior space,
a second well in the transducer base that receives a miniaturized second pressure sensor assembly therein, the second sensor assembly including a second electrical connection to deliver a second pressure signal to the display and a second sensor membrane in fluid communication with a second pressure lumen that extends from the second sensor membrane through the catheter shaft to a channel through the shaft and into the interior space of the second pressure sensing balloon, and wherein the second sensor assembly is secured in the second well so as to maintain a fluid-tight seal between the second pressure lumen and the second sensor membrane and wherein the second pressure lumen and the interior space of the second pressure-sensing balloon include a second prefilled charge of fluid therein.

3. The pressure sensing catheter as set forth in claim 2 wherein each of the first pressure and the second pressure lumen are arranged in an offset with respect to, and parallel to, a central longitudinal axis of the catheter shaft.

4. The pressure sensing catheter as set forth in claim 3 wherein the transducer base includes a first base pressure lumen extending between the first sensor membrane and the first pressure lumen of the catheter shaft and a second base pressure lumen extending between the second sensor membrane and the second pressure lumen of the catheter shaft.

5. The pressure sensing catheter as set forth in claim 4 wherein the first well and the second well are located along a proximal base face of the transducer base, the proximal base face extending along a plane approximately perpendicular to the central longitudinal axis.

6. The pressure sensing catheter as set forth in claim 4 further comprising an infusion/flushing lumen arranged in an offset with respect to, and parallel to, the central longitudinal axis of the catheter shaft, the infusion/flushing lumen communicating with a fluid-source interconnection extending from the transducer base and an outlet port adjacent to the distal end of the catheter shaft.

7. The pressure sensing catheter as set forth in claim 6 wherein the infusion/flushing lumen includes a base infusion/flushing lumen in communication between the catheter shaft and the fluid-source interconnection.

8. The pressure sensing catheter as set forth in claim 7 wherein the first well and the second well are located along a proximal base face of the transducer base, the proximal base face extending along a plane approximately perpendicular to the central longitudinal axis, and further comprising an external infusion/flushing interconnection, connected to the base infusion/flushing lumen and extending proximally from the proximal base face between each of the first well and the second well.

9. The pressure sensing catheter as set forth in claim 1 further comprising an infusion/flushing lumen arranged in an offset with respect to, and parallel to, the first pressure lumen in the catheter shaft, the infusion/flushing lumen communicating with a fluid-source interconnection extending from the transducer base and an outlet port adjacent to the distal end of the catheter shaft.

10. The pressure sensing catheter as set forth in claim 9 wherein the transducer base includes a first base pressure lumen extending between the first sensor membrane and the first pressure lumen of the catheter shaft and a base infusion/flushing lumen in communication between the catheter shaft and the fluid-source interconnection.

11. The pressure sensing catheter as set forth in claim 1 wherein the transducer base includes a cylindrical extension that supports the first sensor membrane, the cylindrical extension including a sealing ring that engages the first well to form the fluid-tight seal between the first pressure lumen and the first sensor membrane, the first well further including a fluid reservoir between the first pressure lumen and the first sensor membrane.

12. A pressure sensing catheter comprising:
a catheter shaft having a proximal end, a distal end and a pressure sensing lumen extending between the proximal and distal ends of the catheter shaft;
at least one pressure sensing balloon located on the catheter shaft near to the distal end of the catheter shaft;
the pressure sensing balloon being sealed to the catheter shaft and defining with the catheter shaft a fluid-tight interior space that is in fluid communication with the pressure sensing lumen of the catheter shaft;
a transducer base attached to the proximal end of the catheter shaft;
the transducer base forming a fluid-tight seal with the proximal end of the catheter shaft;
a pressure sensor assembly supported by the transducer base and comprised of a transducer for converting a pressure signal into an electrical signal for coupling to a display;
the pressure sensor assembly forming a fluid-tight seal with the transducer base;
a prefilled charge of fluid disposed in the pressure sensing lumen of the catheter shaft and the fluid-tight interior space of the pressure sensing balloon;
the pressure sensing lumen of the catheter shaft, the fluid-tight interior space of the pressure sensing balloon and the pressure sensor assembly forming a passive closed pressure system having the prefilled charge of fluid.

13. The pressure sensing catheter as set forth in claim 12 including a well in the transducer base that receives the pressure sensor assembly therein.

14. The pressure sensing catheter as set forth in claim 13 wherein the pressure sensor assembly includes an electrical connection to deliver a pressure signal to the display.

15. The pressure sensing catheter as set forth in claim 14 wherein the pressure sensor assembly includes a sensor membrane in fluid communication with the pressure sensing lumen.

16. The pressure sensing catheter as set forth in claim 12 including a port in the catheter shaft for fluid communication between the catheter shaft and pressure sensing balloon.

17. The pressure sensing catheter as set forth in claim 16 wherein the catheter shaft ort extends radially.

18. The pressure sensing catheter as set forth in claim 12 further comprising a second pressure sensing balloon located on the catheter shaft near to the distal end of the catheter shaft and spaced-apart therealong from the at least one pressure sensing balloon.

19. The pressure sensing catheter as set forth in claim 18 wherein the second pressure sensing balloon is sealed to the catheter shaft so as to define a fluid-tight interior space.

20. The pressure sensing catheter as set forth in claim 19 including a second well in the transducer base that receives a second pressure sensor assembly therein, the second sensor assembly including an electrical connection to deliver a second pressure signal to the display and a second sensor membrane in fluid communication with a second pressure lumen that extends from the second sensor membrane through the catheter shaft to the interior space of the second pressure sensing balloon.

* * * * *